United States Patent
Varghese et al.

(10) Patent No.: US 11,596,323 B2
(45) Date of Patent: Mar. 7, 2023

(54) DETERMINING A WATER AND A LIPID LEVEL OF SKIN

(71) Applicant: KONINKLIJKE PHILIPS N.V., Eindhoven (NL)

(72) Inventors: Babu Varghese, Eindhoven (NL); Wouter Hendrik Cornelis Spoorendonk, Deventer (NL); Walter Hermans, Overpelt (BE); Marco Baragona, Delft (NL); Anna Ezerskaya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 318 days.

(21) Appl. No.: 16/957,125

(22) PCT Filed: Dec. 27, 2018

(86) PCT No.: PCT/EP2018/097029
§ 371 (c)(1),
(2) Date: Jun. 23, 2020

(87) PCT Pub. No.: WO2019/129812
PCT Pub. Date: Jul. 4, 2019

(65) Prior Publication Data
US 2020/0345263 A1    Nov. 5, 2020

(30) Foreign Application Priority Data
Dec. 27, 2017    (EP) ..................................... 17210608

(51) Int. Cl.
*A61B 5/05*    (2021.01)
*A61B 5/0537*    (2021.01)
(Continued)

(52) U.S. Cl.
CPC .......... *A61B 5/0537* (2013.01); *A61B 5/1477* (2013.01); *A61B 5/443* (2013.01);
(Continued)

(58) Field of Classification Search
CPC ..... A61B 5/0537; A61B 5/1477; A61B 5/443; A61B 5/486; A61B 5/4872; A61B 5/4875; A61B 5/4272; A61B 5/6801
See application file for complete search history.

(56) References Cited

U.S. PATENT DOCUMENTS

| 4,966,158 A | 10/1990 | Honma |
| 5,738,107 A | 4/1998 | Martinsen |

(Continued)

FOREIGN PATENT DOCUMENTS

| JP | H09243683 | 9/1997 |
| JP | 2007181524 | 7/2007 |

(Continued)

OTHER PUBLICATIONS

International Search Report and Written Opinion dated May 13, 2019 for International Application No. PCT/EP2018/097029 Filed Dec. 27, 2018.

(Continued)

*Primary Examiner* — Rex R Holmes

(57) ABSTRACT

There is provided a system (100) and method for determining a water or lipid level of skin. The system (100) comprises at least two electrodes (108) suitable for contacting skin, and a signal generator (106) configured to generate an electrical signal at a frequency across the at least two electrodes (108). The system (100) is configured to measure a conductivity between the at least two electrodes (108). The system (100) is further configured to determine a water or lipid level of skin based on the measured conductivity and the frequency of the electrical signal.

8 Claims, 4 Drawing Sheets

(51) Int. Cl.
A61B 5/1477 (2006.01)
A61B 5/00 (2006.01)
(52) U.S. Cl.
CPC ............ *A61B 5/486* (2013.01); *A61B 5/4872* (2013.01); *A61B 5/4875* (2013.01)

(56) References Cited

U.S. PATENT DOCUMENTS

| | | | |
|---|---|---|---|
| 7,783,344 B2* | 8/2010 | Lackey | A61B 5/6804 600/547 |
| 2003/0214311 A1 | 11/2003 | Alanen | |
| 2007/0027402 A1 | 2/2007 | Levin | |
| 2010/0298680 A1 | 11/2010 | Talary | |
| 2011/0144525 A1 | 6/2011 | Megej | |
| 2013/0123629 A1 | 5/2013 | Rosenberg | |
| 2017/0007151 A1* | 1/2017 | Rutkove | A61B 5/053 |
| 2018/0103891 A1* | 4/2018 | Moon | A61B 5/0531 |

FOREIGN PATENT DOCUMENTS

| | | |
|---|---|---|
| WO | 2009/004001 | 1/2009 |
| WO | 2011106792 | 9/2011 |
| WO | 2014/098363 | 6/2014 |
| WO | 2016/208932 | 12/2016 |
| WO | 2017005628 | 1/2017 |

OTHER PUBLICATIONS

Gabriel, et al: "Electrical conductivity of tissue at frequencies below 1 MHz", Physics in Medicine and Biology, Institute of Physics Publishing, Bristol GB, vol. 54, No. 16, Aug. 21, 2009.
Gabriel, et al: "The dielectric properties of biological tissues: III Parametric models for the dielectric spectrum oftissues", Physics in Medicine and Biology, vol. 41, No. 11, Nov. 1, 1996.
Written Opinion of the International Preliminary Examining Authority dated Nov. 28, 2019 for for International Application No. PCT/EP2018/097029 Filed Dec. 27, 2018.
International Preliminary Report on Patentability dated Mar. 20, 2020 for for International Application No. PCT/EP2018/097029 Filed Dec. 27, 2018.
Joines et al: "Frequency-Dependent Absorption of Electromagnetic Energy in Biological Tissue", IEEE Transactions on Biomedical Engineering, vol. BME-31, No. 1, Jan. 1984.
Blank: "Further observations on factors which influence the water content of the stratum corneum," J. Invest. Dermatol. 21(4), 259-271 (1953).
Blank: "Factors which influence the water content of the stratum corneum," J. Invest. Dermatol. 18(6), 433-440 (1952).
Addor, et al:, "Skin barrier in atopic dermatitis," An. Bras. Dermatol. 85(2), 184-194 (2010).
Werner, et al: "The water content of the stratum corneum in patients with atopic dermatitis" Measurement with the Corneometer CM 420, Acta Derm. Venereol. 66(4), 281-284 (1986).
Stamatas, et al: "Development of a non-Invasive optical method for assessment of skin barrier to external penetration", Biomedical Optics and 3-D Imaging, OSA Technical Digest, JM3A.42 Optical Society of America, (2012), abstract.
Werner, et al: "Transepidermal water loss in dry and clinically normal skin in patients with atopic dermatitis," Acta Derm. Venereol. 65(2), 102-105 (1985).
Takada, et al: "Noninvasive in Vivo Measurement of Natural Moisturizing Factor Content in Stratum Corneum of Human Skin by Attenuated Total Reflection Infrared Spectroscopy," Appl. Spectrosc. 66(1), 26-32 (2012).
Imokawa, et al: "Stratum corneum lipids serve as a bound-water modulator," J. Invest. Dermatol. 96(6), 845-851 (1990).
Eberlein-König, et al: "Skin Surface pH, Stratum corneum Hydration, Trans-epidermal water loss and skin roughness related to atopic eczema and skin dryness in a population of primary school children," Acta Derm Venereol 2000; 80: 188-191.
Kim, et al: "Evaluation of the degree of skin dryness and the effect of moisturizing therapy in scalp psoriasis", Annual Global Pharma Summit, Philadelphia, USA (2015).
Tomita, et al: "Stratum corneum hydration and flexibility are useful parameters to indicate clinical severity of congenital ichthyosis," Exp. Dermatol. 14(8), 619-624 (2005).
Lavrijsen, et al: "Reduced skin barrier function parallels abnormal stratum corneum lipid organization in patients with Lamellar Ichthyosis," J. Invest. Dermatol. 105(4), 619-624 (1995).
Bouwstra, et al: "Structure of the skin barrier and its modulation by vesicular formulations," Prog. Lipid Res. 42(1), 1-36 (2003).
Zhang, et al: "In vivo comparative documentation of skin hydration by confocal Raman microscopy," Proc. SPIE 7548, 75480M (2010).

* cited by examiner

| Frequency | Frequency | Range | WET SKIN/LIPID | WET SKIN/DRY SKIN | DRY SKIN/LIPID | Sensitivity |
|---|---|---|---|---|---|---|
| f1 | 50 Hz | 10-500 Hz | 0,01 | 2,74 | 0,01 | Lipid |
| f2 | 50 kHz | 10-100 kHz | 0,92 | 57,48 | 0,02 | Water |
| f3 | 1 MHz | 0,8-5 MHz | 10,80 | 10,71 | 1,01 | Water |
| f4 | 50 MHz | 10-100 MHz | 17,14 | 1,42 | 12,04 | Lipid |

DETERMINING A WATER AND A LIPID LEVEL OF SKIN

CROSS REFERENCE TO RELATED APPLICATIONS

This application is the U.S. National Phase application under 35 U.S.C. § 371 of International Application No. PCT/EP2018/097029 filed Dec. 27, 2018, published as WO 2019/129812 on Jul. 4, 2019, which claims the benefit of European Patent Application Number 17210608.0 filed Dec. 27, 2017. These applications are hereby incorporated by reference herein.

FIELD OF THE INVENTION

The invention relates to a system and method for determining a water or lipid level of skin.

BACKGROUND OF THE INVENTION

Skin surface lipid (e.g. sebum) and water (e.g. hydration) levels are considered important factors in determining skin appearance and skin health. The right balance between these components is an indication of healthy skin and plays a central role in protecting and preserving skin integrity. Hydration and lipid retaining ability of the skin is primarily related to the stratum corneum (SC). The SC plays the role of the barrier to water loss and is composed of the corneocyte and an intercellular lipid bilayer matrix. The water retaining property of the SC is dependent on (i) the presence of natural hygroscopic agents collectively referred to as natural moisturizing factor (NMF) and (ii) the SC intercellular lipids orderly arranged to form a barrier to prevent transepidermal water loss.

Generally, skin remains flexible when it contains 10-20% water, but becomes brittle, when it drops below 10%. Skin lipids (e.g. sebum) are a mixture of fatty acids, triglycerides, proteins, and other molecules produced by the sebaceous glands in the dermis. Skin lipids keep skin smooth and flexible by sealing and preserving moisture in the corneal layer and preventing evaporation and bacterial infections. The sebum excretion rate (SER) reflects the amount of lipid (e.g. sebum) production and is closely related to the physiological activities of the sebaceous glands. This is important information in the pathogenesis of sebaceous glands disorders and pimple and acne.

An optimal balance between lipid and water level provides the skin with a radiant, smooth texture and a natural pigmentation appearance, which is important from a cosmetic perspective. Excessive lipid production can cause clogged pores possibly resulting in blemishes. Sufficient amount of skin hydration and lipids makes the skin appear smooth, soft and supple whereas lack of moisture can cause the skin to look dull and cracked, appearing older. The reduction in the efficiency of the barrier and moisture maintaining functions of the skin result in easily dried, roughened skin which can be potentially more vulnerable to risk of infection.

PCT patent application WO 2016/208932 A1 discloses a skin condition measuring device which is arranged to measure skin moisture and skin oiliness by applying an alternating current to the skin and measuring a return alternating current. According to this patent application the skin moisture might be derived from the resistance measured and the skin oiliness might be derived from the shape of the measured return alternating current. Allegedly the skin moisture and skin oiliness may be derived by using one input signal only.

SUMMARY OF THE INVENTION

As noted above, water and lipid content are important factors in determining overall skin health and there exist hydration measuring devices that measure, for example, the capacitance or current conductivity of the skin and detect moisture on the skin based on these measurements. However, it has been observed by the inventors herein that these measurements may in fact depend on both the water (e.g. hydration) level and lipid (e.g. oil) level of the skin, which can result in inaccuracies in such devices. For example, hydration levels measured with such devices may change depending on the surface lipid level of the skin, even if two patches of identically hydrated skin are measured. It is therefore desirable to provide a system and method for determining a level of water or lipid content of the skin.

According to a first aspect there is provided a system for determining a water and a lipid level of skin The system comprises at least two electrodes suitable for contacting skin and a signal generator configured to generate an electrical signal at a frequency across the at least two electrodes. The system is configured to measure a conductivity between the at least two electrodes and determine a water or lipid level of skin based on the measured conductivity and the frequency of the electrical signal.

The signal generator may be configured to generate an electrical signal at a first frequency in a first frequency range. The system is configured to determine a water level of skin based on the measured conductivity when the frequency of the signal is the first frequency.

The first frequency range is a frequency range from 10 kHz to 100 kHz or a frequency range from 0.8 MHz to 5 MHz.

In some embodiments, the first frequency may be 50 kHz or 1 MHz.

In some embodiments, the signal generator may be configured to generate an electrical signal at a second frequency in a second frequency range. In these embodiments, the system may be configured to determine a lipid level of skin based on the measured conductivity when the frequency of the signal is the second frequency.

The second frequency range is different to the first frequency range.

The second frequency range is a frequency range from 10 Hz to 500 Hz or a frequency range from 10 MHz to 100 MHz.

In some embodiments, the second frequency may be 50 Hz or 50 MHz.

In some embodiments, the system may be configured to measure the conductivity at a plurality of frequencies to acquire a plurality of conductivity measurements.

In some embodiments, the system may be configured to determine a water or lipid level of skin by determining an average water or lipid level of skin from the plurality of conductivity measurements.

The system is further configured to compare the measured conductivity to one or more predefined profiles describing the manner in which skin conductivity varies with frequency, and determine a water or lipid level of skin based on the comparison of the measured conductivity and the frequency of the radio frequency signal.

In some embodiments, the system may be further configured to determine a skin condition based on the determined water or lipid level.

In some embodiments, the system may be further configured to determine a recommendation for a skin treatment based on the determined skin condition.

According to a second aspect, there is provided a method of operating a system to determine a water or lipid level of skin.

The system comprises at least two electrodes suitable for contacting skin and a signal generator configured to generate an electrical signal across the at least two electrodes at a frequency. The method comprises measuring a conductivity between the at least two electrodes, and determining a water or lipid level of skin based on the measured conductivity and the frequency of the electrical signal.

According to a third aspect, there is provided a computer program product comprising a non-transitory computer readable medium, the computer readable medium having computer readable code embodied therein, the computer readable code being configured such that, on execution by a suitable computer or processor, the computer or processor is caused to perform the method as described above.

According to the aspects and embodiments described above, it is possible to measure the water level of skin substantially independently of its lipid level and/or to measure the lipid level of skin substantially independently of its water level, by taking into account the frequency of the electrical signal in the determination of water or lipid level from the measured conductivity. More specifically, by determining a water or lipid level based on the measured conductivity and the frequency of the electrical signal, a conductivity measurement may be made at a frequency that is more sensitive to the property being measured (e.g. water or lipid level). In this way, more accurate measurements of the water or lipid level of skin can be determined. Moreover, it is possible for the water and lipid level of skin to be determined using a single system (e.g. a single device). The system and corresponding method can be used to enable assessment of the balance between water and lipid level, which is related to skin health and thus can be used in the selection of appropriate skin care treatments and products. The systems and method can further be used in monitoring the progress of such treatment.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

As noted above, there is provided a system and method for determining a level of water (or hydration) and of lipid (or sebum or oil) content of the skin.

Figure 1:
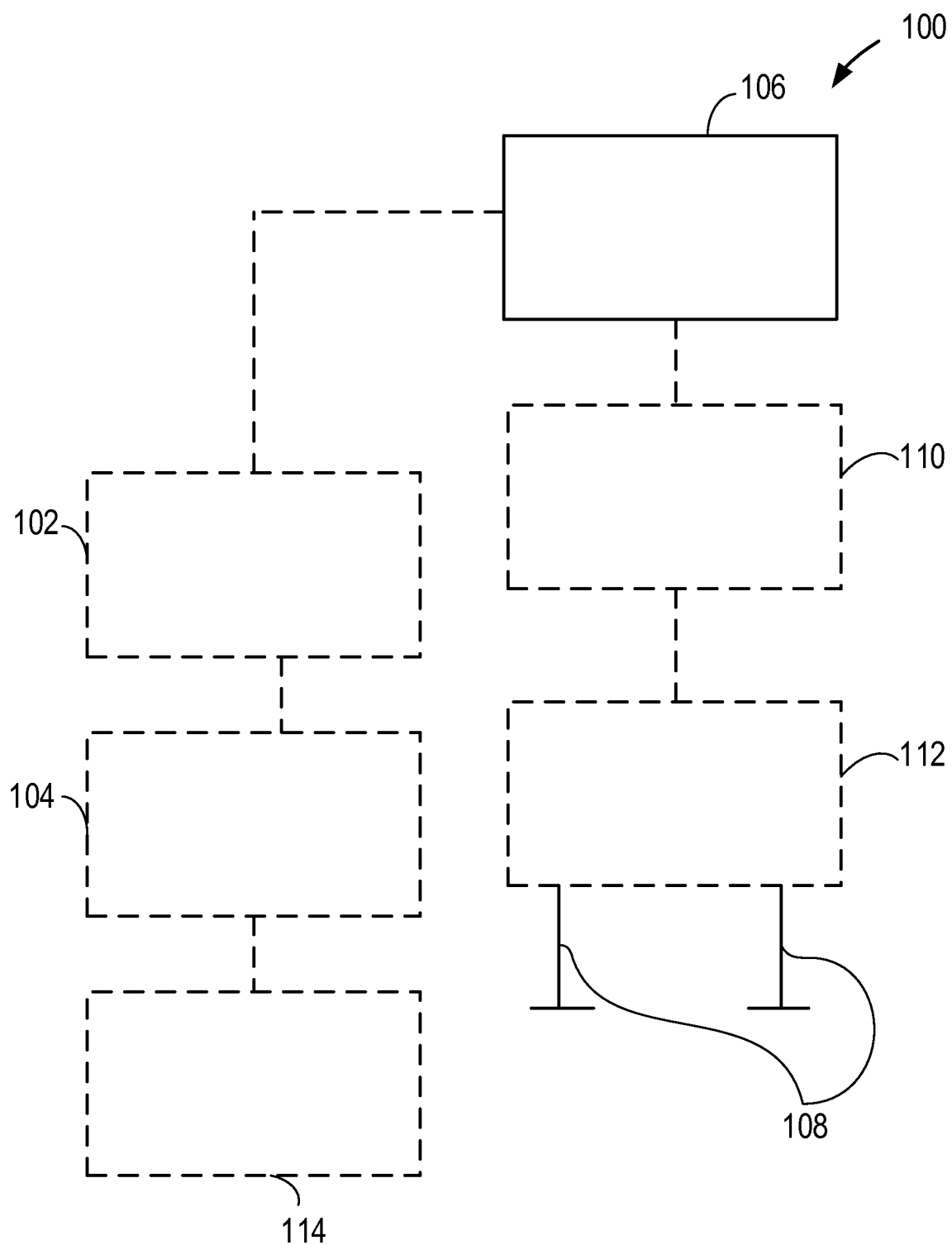
FIG. 1 is an illustration of a system according to an embodiment herein.

FIG. 1 shows a system 100 for determining a water or lipid level of skin. The system comprises at least two (for example, at least one pair of) electrodes 108 suitable for contacting skin, and a signal generator 106 configured to generate an electrical signal at a frequency across the at least two electrodes 108. In some embodiments, the system 100 described herein may be a device. Briefly, the system 100 is configured to measure a conductivity between the at least two electrodes 108, and determine a water or lipid level of skin based on the measured conductivity and the frequency of the electrical signal. In use, the at least two electrodes and the skin form an electrical circuit. The electrical signal generated across the at least two electrodes 108 thus passes through the skin between the at least two electrodes 108 such that the conductivity of skin can be measured.

In some embodiments, the at least two electrodes 108 may comprise at least one active electrode configured to transmit the electrical signal and at least one corresponding return electrode configured to receive the electrical signal transmitted from the at least one active electrode. In some embodiments, the at least two electrodes 108 can comprise at least two microelectrodes. An electrode of the at least two electrodes 108 may be located at any suitable distance from another of the at least two electrodes 108. For example, in some embodiments, electrodes may be located at a distance in a range from 0.1 mm to 1 mm from each other. In this way, the sensitivity of the system 100 may be increased, such as to measure skin superficial layers.

As noted above, it has been observed by the inventors herein, that the conductivity of the skin may depend on both water and lipid levels, which may result in inaccuracies in measurements of hydration levels acquired using existing devices. By determining a water or lipid level based on the measured conductivity and the frequency of the electrical signal, a conductivity measurement may be made at a frequency that is more sensitive to the property being measured (e.g. water or lipid level). In this way, more accurate measurements of the water or lipid content of the skin can be determined.

A person skilled in the art will be familiar with electrodes suitable for contacting skin. In some embodiments, a pad (or patch) may comprise the at least two electrodes 108 and the pad may be suitable for contacting skin. For example, each electrode may be partially embedded in a pad. In some embodiments, the at least two electrodes 108 (or a pad comprising the at least two electrodes 108) may comprise an adhesive surface that enables the at least two electrodes 108 (or pad comprising the at least two electrodes 108) to be adhered to skin. In some embodiments, the at least two electrodes 108 may comprise an array of electrodes. In some embodiments, the at least two electrodes 108 (or the array of electrodes) may be configured (or arranged) to cover an area of interest on the skin. For example, an array of electrodes may be used to measure the conductivity of a larger area of skin for large area mapping of skin conditions. In some embodiments, an array of electrodes may be comprised in, for example, a fingerprint sensor.

As mentioned earlier, the signal generator 106 of the system 100 is configured to generate an electrical signal at a frequency across the at least two electrodes 108. In some embodiments, the signal generator 106 may be configured to generate frequency pulses. The frequency pulses may, for example, be fixed frequency pulses or variable frequency pulses. In some embodiments, the pulses may comprise low-voltage pulses. In some embodiments, the signal generator 106 may be configured to generate a radiofrequency (RF) signal. Thus, in some embodiments where the signal generator 106 is configured to generate frequency pulses, the pulses may comprise radiofrequency pulses.

As illustrated in FIG. 1, in some embodiments, the system 100 may further comprise an amplifier 110 (such as a radiofrequency amplifier). In some embodiments, the amplifier 110 may amplify the voltage output by the signal generator 106. As illustrated in FIG. 1, in some embodiments, the system 100 may further comprise a conductance measurement system (such as an impedance measurement system) 112. The conductance measurement system 112 may, for example, measure the voltage across the at least two electrodes 108. When the at least two electrodes 108 are in contact with skin (e.g. when the system is in use), the conductance measurement system 112 may measure the current flowing through the circuit formed by the at least two electrodes 108 of the system 100 and the skin. The conductivity measurement system 112 can be configured to measure the conductivity between the electrodes from the measured current. A person skilled in the art will be aware of the manner in which conductivity can be derived from a measured current.

In some embodiments, the system 100 may be implemented mechanically, for example, the conductivity measured between the electrodes may be displayed on an analogue display. Such an analogue display may be calibrated (e.g. the scale may be shifted or scaled) such that the analogue display displays water or lipid level.

In other embodiments, as shown in FIG. 1, the system 100 may further comprise a processor 102. The processor 102 may, for example, be configured to control the signal generator 106 to generate an electrical signal at the frequency across the at least two electrodes 108. For example, the processor 102 may be suitable for controlling the signal generator 106 to generate pulses of a desired frequency, voltage and/or pulse duration. In some embodiments, the conductance measurement system 112 may be controlled by the processor 102. Alternatively or in addition, in some embodiments, the output of the conductance measurement system 112 may be sent to the processor 102 for subsequent processing and/or output (e.g. display to a user).

Generally, in embodiments where the system 100 comprises a processor 102, the processor 102 may control the operation of the system 100 to implement the method described herein. The processor 102 can be implemented in numerous ways, with software and/or hardware, to perform the various functions described herein. In particular implementations, the processor 102 can comprise a plurality of software and/or hardware modules, each configured to perform, or that are for performing, individual or multiple steps of the method described herein. The processor 102 can comprise one or more processors (such as one or more microprocessors, one or more multi-core processors and/or one or more digital signal processors (DSPs)), one or more processing units and/or modules, and/or one or more controllers (such as one or more microcontrollers) that may be configured or programmed (e.g. using software or computer program code) to control or operate the system 100 in the manner described herein.

In some implementations, for example, the processor 102 may comprise a plurality of (for example, interoperated) processors, processing units and/or modules, multi-core processors and/or controllers configured for distributed processing. It will be appreciated by a person skilled in the art that such processors, processing units and/or modules, multi-core processors and/or controllers may be located in different locations and may perform different steps and/or different parts of a single step of the method described herein. The processor 102 may be implemented as a combination of dedicated hardware (e.g. amplifiers, pre-amplifiers, analog-to-digital convertors (ADCs) and/or digital-to-analog convertors (DACs)) to perform some functions and a processor (e.g. one or more programmed microprocessors, controllers, DSPs and associated circuitry) to perform other functions.

As illustrated in FIG. 1, in some embodiments, the system 100 can comprise a memory 104. The memory 104 may comprise instruction data representing a set of instructions. For example, the memory 104 may be configured to store the instruction data in the form of program code that can be executed by the processor 102 to cause the system 100 to operate in the manner described herein. In some implementations, the instruction data can comprise a plurality of software and/or hardware modules that are each configured to perform, or are for performing, individual or multiple steps of the method described herein. In some embodiments, the memory 104 may be part of a device that also comprises one or more other components of the system 100 (for example, the processor 102 and/or one or more other components of the system 100). In alternative embodiments, the memory 104 may be part of a separate device to the other components of the system 100.

In some embodiments, the memory 104 may comprise a plurality of sub-memories, each sub-memory being capable of storing a piece of instruction data. In some embodiments where the memory 104 comprises a plurality of sub-memories, instruction data representing the set of instructions may be stored at a single sub-memory. In other embodiments where the memory 104 comprises a plurality of sub-memories, instruction data representing the set of instructions may be stored at multiple sub-memories. For example, at least one sub-memory may store instruction data representing at least one instruction of the set of instructions, while at least one other sub-memory may store instruction data representing at least one other instruction of the set of instructions. Thus, according to some embodiments, the instruction data representing different instructions may be stored at one or more different locations in the system 100. In some embodiments, the memory 104 may be used to store information, data, signals (e.g. conductivity signals) and measurements (e.g. conductivity measurements) acquired or made by the system 100, such as the processor of the system 100 or any other components of the system 100.

The memory may comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM), and electrically erasable PROM (EEPROM).

The processor 102 of the system 100 can be configured to communicate with the memory 104 to execute the set of instructions. The set of instructions, when executed by the processor 102 may cause the processor 102 to perform the method described herein.

Returning again to FIG. 1, in some embodiments, the system 100 may comprise at least one user interface 114. In some embodiments, the user interface 114 may be part of a device that also comprises one or more other components of the system 100 (for example, the processor 102, the memory 104 and/or one or more other components of the system 100). In alternative embodiments, the user interface 114 may be part of a separate device to the other components of the system 100.

A user interface 114 may be for use in providing a user of the system 100 (for example, a medical professional, a dermatologist, a user in a home setting, or any other user of the system 100) with information resulting from the method according to embodiments herein. The set of instructions, when executed by the processor 102 may cause the processor 102 to control one or more user interfaces 114 to provide information resulting from the method according to embodiments herein. For example, according to some embodiments, the user interface 114 may be configured to render (for example, provide, output or display) the water or lipid level of skin determined by the system 100. Alternatively or in addition, a user interface 114 may be configured to receive a user input. In other words, a user interface 114 may allow a user of the system 100 to manually enter instructions, data, or information. The set of instructions, when executed by the processor 102 may cause processor 102 to acquire the user input from one or more user interfaces 114.

A user interface 114 may be any user interface that enables rendering (or output or display) of information, data or signals to a user of the system 100. Alternatively or in addition, a user interface 114 may be any user interface that enables a user of the system 100 to provide a user input, interact with and/or control the system 100. For example, the user interface 114 may comprise one or more switches, one or more buttons, a keypad, a keyboard, a mouse, a mouse wheel, a touch screen or an application (for example, on a tablet or smartphone), a display screen, a graphical user interface (GUI) or other visual rendering component, one or more speakers, one or more microphones or any other audio component, one or more lights, a component for providing tactile feedback (e.g. a vibration function), or any other user interface, or combination of user interfaces.

It will be appreciated that FIG. 1 only shows the components required to illustrate this aspect of the disclosure and, in a practical implementation, the system 100 may comprise additional components to those shown. For example, the system 100 may comprise a battery or other power supply for powering the system 100 or means for connecting the system 100 to a mains power supply. The system 100 may further comprise a communications interface (or circuitry) for enabling the system 100 (or components of the system 100) to communicate with components, interfaces, memories and/or devices that are part of the system 100 or that at external to (i.e. separate from or remote to) the system 100. Such a communications interface may communicate with any components, interfaces, memories and devices wirelessly, via a wired connection, or via any other communication (or data transfer) mechanism. In some wireless embodiments, the communications interface may, for example, use radiofrequency (RF), Bluetooth, or any other wireless communication technologies, for communications.

As described briefly above, the system 100 is configured to measure a conductivity between the at least two electrodes 108 and determine a water or lipid level of skin based on the measured conductivity and the frequency of the electrical signal.

The signal generator 106 is configured to generate an electrical signal at a first frequency and an electrical signal at a second frequency and the system 100 may be configured to measure a water level when the generated electrical signal is at the first frequency and a lipid level when the generated electrical signal is at the second frequency.

Thus, the value of the frequencies used to make the determination may depend on whether the system is to determine a water or lipid level. As noted above, it has been observed experimentally by the inventors herein that the conductivity of skin is dependent on both the lipid and water content of the skin.

Figure 2:
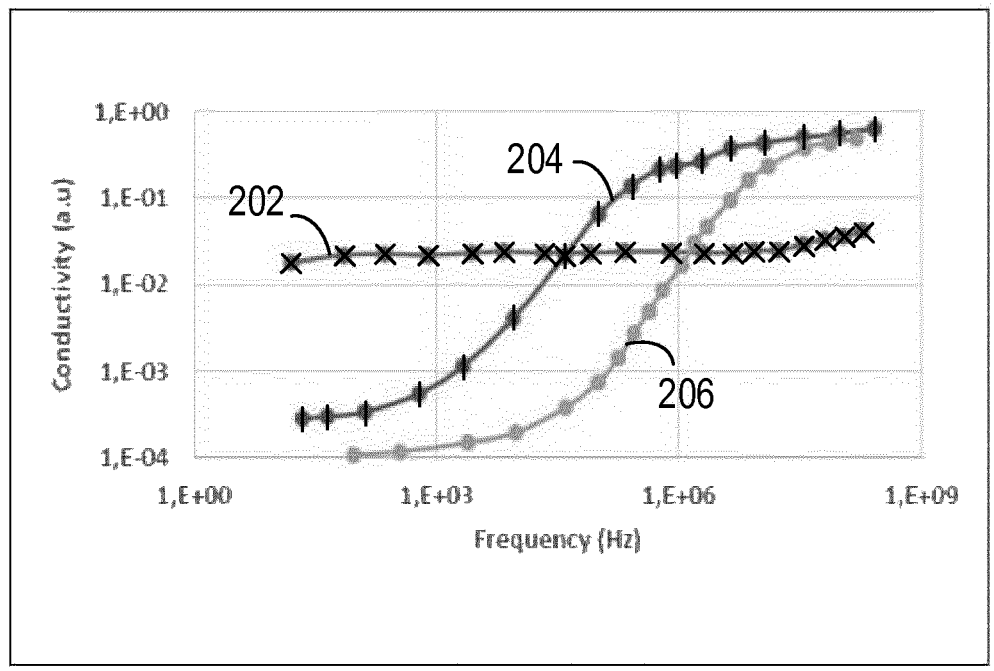
FIG. 2 shows a graph of frequency versus skin conductivity for different skin types.

FIG. 2 shows a plot of conductivity with respect to (or versus or as a function of) frequency for breast tissue 202 (e.g. tissue high in lipids), wet skin 204 and dry skin 206 respectively. From FIG. 2, various ratios of conductivity may be determined that may be used to ascertain the frequency ranges (e.g. frequency bands) most sensitive to (and thus most suitable for measuring) water and lipid levels with improved sensitivity.

Figure 3:
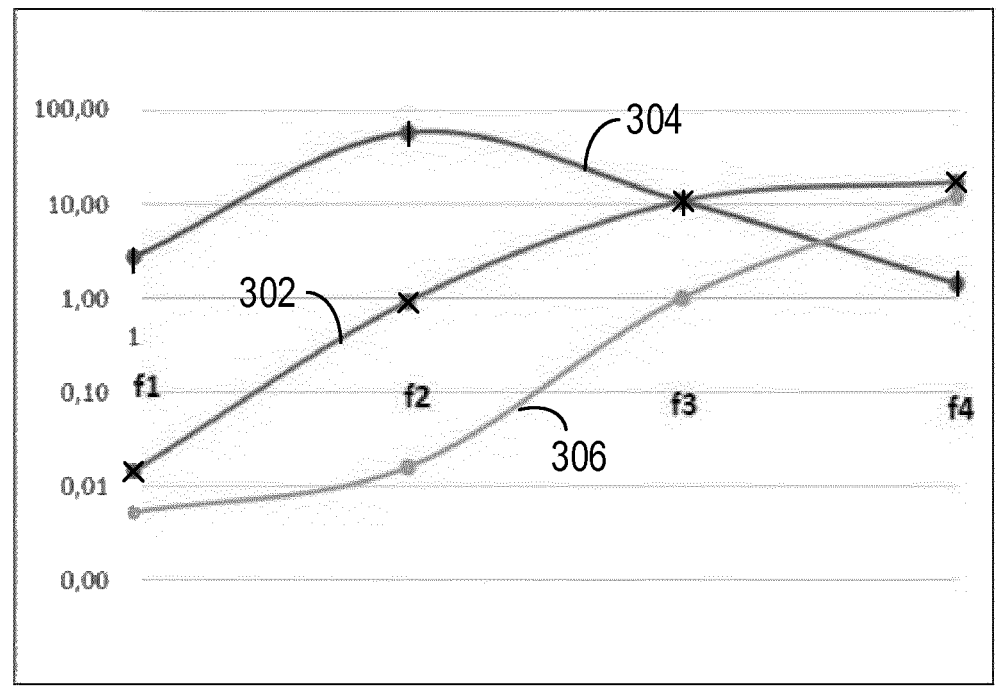
FIG. 3 illustrates ratios of conductivity that compare the conductivity of different skin types with respect to frequency.

FIG. 3 shows ratios of conductivities at different frequencies. The ratio of the conductivity of wet skin to lipid level is shown by line 302, the ratio of wet skin to dry skin is shown by line 304, and the ratio of dry skin to lipid level is shown by line 306. Four frequency ranges f1-f4 may then be defined, each frequency range being more sensitive to (e.g. the value of a conductivity measurement made in said range being more heavily dependent on) either water level or lipid level. Put another way, in these ranges, the contrast between lipid and water level may be optimal for measuring a particular one of water and lipid level. Example frequency ranges suitable for measuring water and lipid levels of the skin are summarized in the table shown in FIG. 4.

Therefore, the frequency of the electrical signal generated by the signal generator 106 determines whether the measured conductivity is indicative of the water or lipid level of skin.

The signal generator 106 is configured to generate an electrical signal at a first frequency in a first frequency range and the system 100 may be configured to determine a water level of skin based on the measured conductivity when the frequency of the signal is the first frequency. The first frequency range may comprise frequencies in which the contrast between the conductivities of wet skin and dry skin is sufficiently high so that measured skin conductivity is sensitive to the water level (or the amount of water). The first frequency range comprises frequencies in which the contrast between the conductivities of lipids and wet or dry skin is lower so that the skin conductivity is less sensitive to the lipid level (or the amount of lipids). As such, in some embodiments, the conductivity is influenced to a greater extent by water than lipid when the frequency of the signal is the first frequency. In this way, the value of the conductivity at the first frequency depends more on (e.g. is more highly dependent on) water content of the skin and thus, the conductivity at the first frequency (or within the first frequency range) may be more accurately used to measure water content than at other frequencies (or frequency ranges).

In some embodiments, the first frequency range may be a frequency range from 10 kHz to 100 kHz, for example a frequency range from 20 kHz to 90 kHz, for example a frequency range from 30 kHz to 80 kHz, for example a frequency range from 40 kHz to 70 kHz, for example a frequency range from 50 kHz to 60 kHz. In some embodiments, for example, the first frequency may be a frequency selected from 10 kHz, 20 kHz, 30 kHz, 40 kHz, 50 kHz, 60 kHz, 70 kHz, 80 kHz, and 90 kHz. In other embodiments, the first frequency range may be a frequency range from 0.8 MHz to 5 MHz, for example a frequency range from 1.4 MHz to 4.4 MHz, for example a frequency range from 2 MHz to 3.8 MHz, for example a frequency range from 2.6 MHz to 3.2 MHz. In some embodiments, for example, the first frequency may be a frequency selected from 1 MHz, 2 MHz, 3 MHz, 4 MHz and 5 MHz. In other embodiments, the first frequency range may be a frequency range from 500 kHz to 1 MHz, for example a frequency range from 500 kHz to 0.9 MHz, for example a frequency range from 500 kHz to 0.8 MHz.

Generally, the conductivity measured when the frequency of the electrical signal generated by the signal generator 106 is the first frequency may be used to determine the water level of skin using a relationship between conductivity and water level (e.g. water content). In some embodiments, such a relationship between conductivity and water level may comprise an empirical relationship. In general, the conductivity measured by the signal generator 106 may be converted to a water level using a calibration curve or table. Such empirical relationships, calibration curves and/or tables may be derived by comparing measured skin conductivity to water level. For example, by comparing measured conductivity levels with water level measured using a Confocal Raman micro-spectrometer. In some embodiments, the empirical relationships, calibration curves and/or tables may be stored in the memory 104 of the system 100.

The derivation of the empirical relationships, calibration curves and/or tables can be referred to as a calibration step used to calibrate the system described herein. In general, this calibration step may be performed once for the system and need not be repeated. In some embodiments, the calibration step may be performed on a calibration sample (or phantom). This calibration sample can, for example, be an emulsion made of sebum and water. The sebum and water may be mixed in a known volume fraction, e.g. using an emulsifier so as to achieve uniform mixing properties throughout the sample. In some embodiments, the system may be calibrated to other industrial standards, such as to a Corneometer (e.g. for water level) and a sebumeter (e.g. for lipid level).

The signal generator 106 is further configured to generate an electrical signal at a second frequency in a second frequency range and the system 100 is configured to determine a lipid level of skin based on the measured conductivity when the frequency of the signal is the second frequency.

The second frequency range comprises frequencies in which the contrast between the conductivities of wet skin and dry skin is sufficiently low so that the skin conductivity is less sensitive to the water level (or the amount of water). The second frequency range comprises frequencies in which the contrast between the conductivities of lipids and wet or dry skin is higher so that the skin conductivity is more sensitive to the lipid level (or the amount of lipids). As such, in some embodiments, the conductivity is influenced to a greater extent by lipid than water when the frequency of the signal is the second frequency. In this way the value of the conductivity at the second frequency depends more on (e.g. is more highly dependent on) lipid content of the skin and thus, the conductivity at the second frequency (or within the second frequency range) may be more accurately used to measure lipid content than other frequencies (or frequency ranges).

In some embodiments, the second frequency range may be a frequency range from 10 Hz to 500 Hz, for example a frequency range from 50 Hz to 500 Hz, for example a frequency range from 100 Hz to 450 Hz, for example a frequency range from 150 Hz to 400 Hz, for example a frequency range from 200 Hz to 350 Hz, for example a frequency range from 250 Hz to 300 Hz. In some embodiments, for example, the first frequency may be a frequency selected from 50 Hz, 100 Hz, 150 Hz, 200 Hz, 250 Hz, 300 Hz, 350 Hz, 400 Hz, 450 Hz and 500 Hz. In other embodiments, the second frequency range may be a frequency range from 10 MHz to 100 MHz, for example a frequency range from 20 MHz to 90 MHz, for example a frequency range from 30 MHz to 80 MHz, for example a frequency range from 40 MHz to 70 MHz, for example a frequency range of 50 MHz to 60 MHz. In some embodiments, for example, the second frequency may be a frequency selected from 10 MHz, 20 MHz, 30 MHz, 40 MHz, 50 MHz, 60 MHz, 70 MHz, 80 MHz, 90 MHz, and 100 MHz. Generally, the conductivity measured when the electrical frequency of the signal generated by the signal generator 106 is the second frequency may be used to determine the lipid level of skin using a relationship between conductivity and lipid level (e.g. lipid or sebum content). In some embodiments, such a relationship between conductivity and lipid level may comprise an empirical relationship. In general, the conductivity measured by the signal generator 106 may be converted to a lipid level using a calibration curve or table. Such empirical relationships, calibration curves and/or tables may be derived by comparing measured skin conductivity to lipid level. For example, by comparing measured conductivity levels with lipid level measured using a Confocal Raman micro-spectrometer. In some embodiments, the empirical relationships, calibration curves and/or tables may be stored in the memory 104 of the system 100.

The derivation of the empirical relationships, calibration curves and/or tables can be referred to as a calibration step used to calibrate the system described herein. In general, this calibration step may be performed once for the system and need not be repeated. In some embodiments, the calibration step may be performed on a calibration sample (or phantom). This calibration sample can, for example, be an emulsion made of sebum and water. The sebum and water may be mixed in a known volume fraction, e.g. using an emulsifier so as to achieve uniform mixing properties throughout the sample. In some embodiments, the system may be calibrated to other industrial standards, such as to a Corneometer (e.g. for water level) and a sebumeter (e.g. for lipid level).

Figures 4, 5:
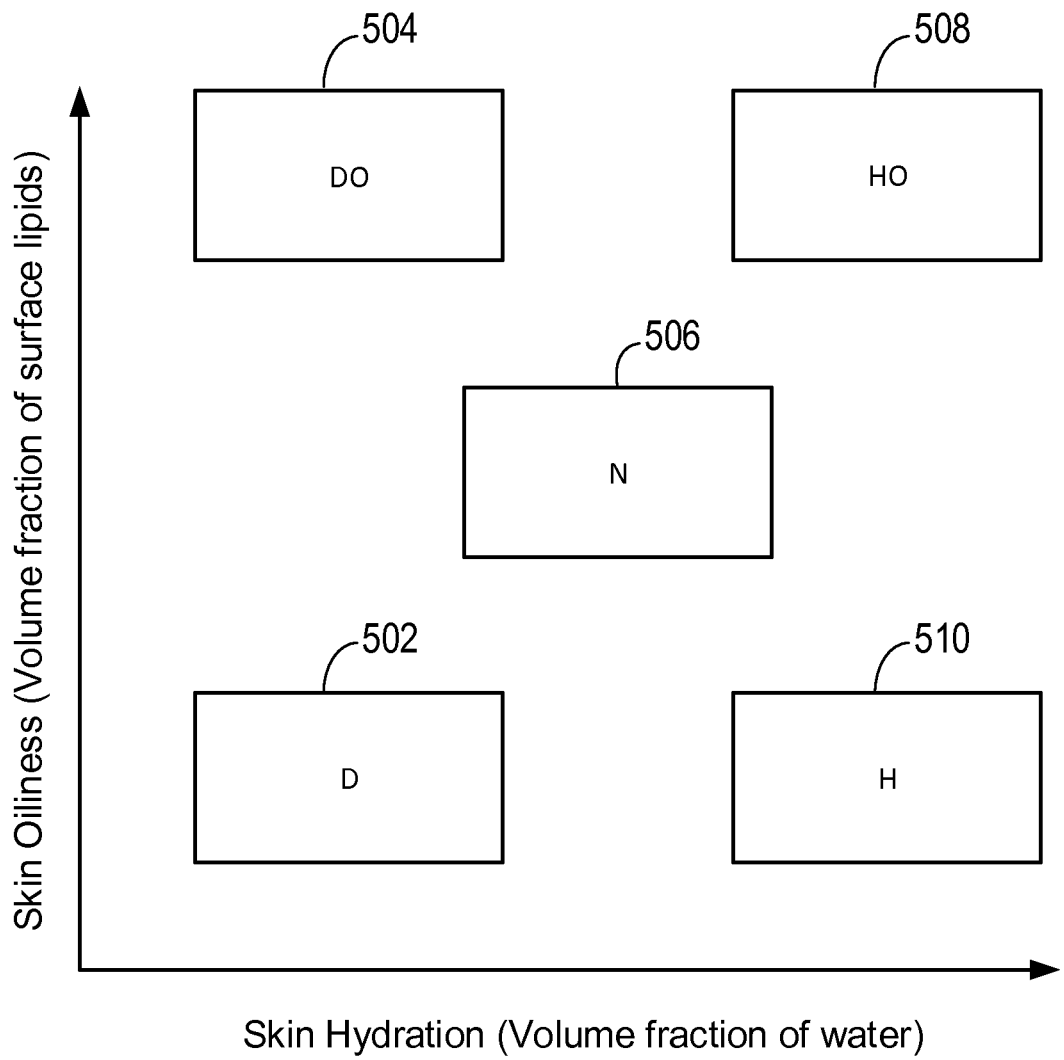
FIG. 4 shows a table of example frequency ranges for determining lipid and water level of skin according to some embodiments.
FIG. 5 illustrates relative lipid and water levels for different skin types according to an embodiment.

The second frequency range referred to herein is different to the first frequency range (or the first frequency is different to the second frequency). In this way, the system 100 can use different frequencies for determining a water level of skin to those used for determining a lipid level of skin, with the conductivity of skin being more highly dependent on (or more influenced by) the water level or lipid level at the first and second frequencies respectively, resulting in more accurate determinations of water and lipid level of the skin. For example, the frequency ranges shown in FIG. 4 are chosen (or selected) so that one of the components (e.g. lipid or water level) can be determined with less confounding influence of the other component.

In some embodiments, the system 100 may be configured to measure the conductivity at a single frequency to acquire a single conductivity measurement. In these embodiments, the single conductivity measurement may be used to determine the water or lipid level of skin. For example, the conductivity measurement may be used to determine the water level of skin when the frequency of the generated electrical signal is the first frequency or the lipid level of skin when the frequency of the generated electrical signal is the second frequency. In other embodiments, the system 100 can be configured to measure the conductivity at a plurality of frequencies to acquire a plurality of conductivity measurements. In these embodiments, the plurality of conductivity measurements may be used to determine the water or lipid level of the skin. For example, a plurality of conductivity measurements acquired when the frequencies of the generated electrical signal are in the first frequency range may be used to determine the water level of the skin and a plurality of conductivity measurements acquired when the frequencies of the generated electrical signal are in the second frequency range may be used to determine the lipid level of the skin.

In some embodiments where a plurality of conductivity measurements are acquired, the system 100 may be configured to determine a water or lipid level of skin by determining an average water or lipid level of skin from the plurality of conductivity measurements. For example, each conductivity measurement of the plurality of conductivity measurements may be used to determine a water level or lipid level of the skin (for example, depending on whether the frequency of the generated electrical signal is in the first frequency range or the second frequency range, as described above). An average of the determined water and/or lipid levels may then be determined.

In some embodiments, a determined lipid level may be used to correct a determined water level. Similarly, in some embodiments, a determined water level may be used to correct a determined lipid level. For example, if it is known that at a particular frequency, lipids contribute to a certain percentage of the value of the measured skin conductivity, and the lipid level is known, then this may be used to determine the amount of the conductivity that can be attributed to water level of the skin (or vice versa).

In some embodiments, the system 100 may be configured to compare the measured conductivity to one or more predefined profiles describing the manner in which skin conductivity varies with frequency, and determine a water or lipid level of skin based on the comparison of the measured conductivity and the frequency of the radio frequency signal.

Examples of predefined profiles are those shown in FIG. 2. FIG. 2 illustrates the manner in which skin conductivity changes with respect to frequency for different skin characteristics (e.g. high lipid content, high water content and low water content). The skilled person will appreciate that FIG. 2 merely shows example profiles and that the measured conductivity levels may be compared to a range of profiles, for example, profiles representing different levels (e.g. different combinations of levels) of water and lipid.

In some embodiments, comparing the measured conductivity (e.g. the plurality of conductivity levels) to one or more predefined profiles can comprise comparing the distribution of conductivity levels to a shape associated with a predetermined profile. For example, the magnitude, slope or first or second derivative of the conductivity measurements may be determined and compared to one or more predetermined profiles to identify whether the conductivity measurements are consistent with the magnitude, slope or first or second derivative of the predetermined profile.

In some embodiments, the water and/or lipid level of the skin may be determined from a best-fitting predetermined profile (e.g. a profile that represents the best-fit to the plurality of conductivity measurements). The skilled person will be familiar with ways to determine a best fitting profile for a plurality of measurements, e.g. such as the least-squares fitting method. In this way, a plurality of conductivity measurements may be fit to a known profile to more accurately determine the water and/or lipid level of the skin.

In any of the embodiments described herein, the system 100 may be further configured to determine a skin condition based on the determined water or lipid level. FIG. 5 shows how the lipid level (e.g. oiliness) and water level (e.g. hydration level) may be used to characterize the skin into one of several types. For example, dry skin 502 is associated with low lipid and low moisture, dry-oily skin 504 with low hydration and high lipid level, normal skin 506 with medium levels of both water and lipid, hydrated oily skin 508 with high lipid level and high levels of water and hydrated skin 510 with high levels of water and low levels of oiliness. In some embodiments, the system 100 may determine a skin condition based on where a determined combination of water and lipid falls on a chart (or in a parameter space) such as that shown in FIG. 5.

Figure 6:
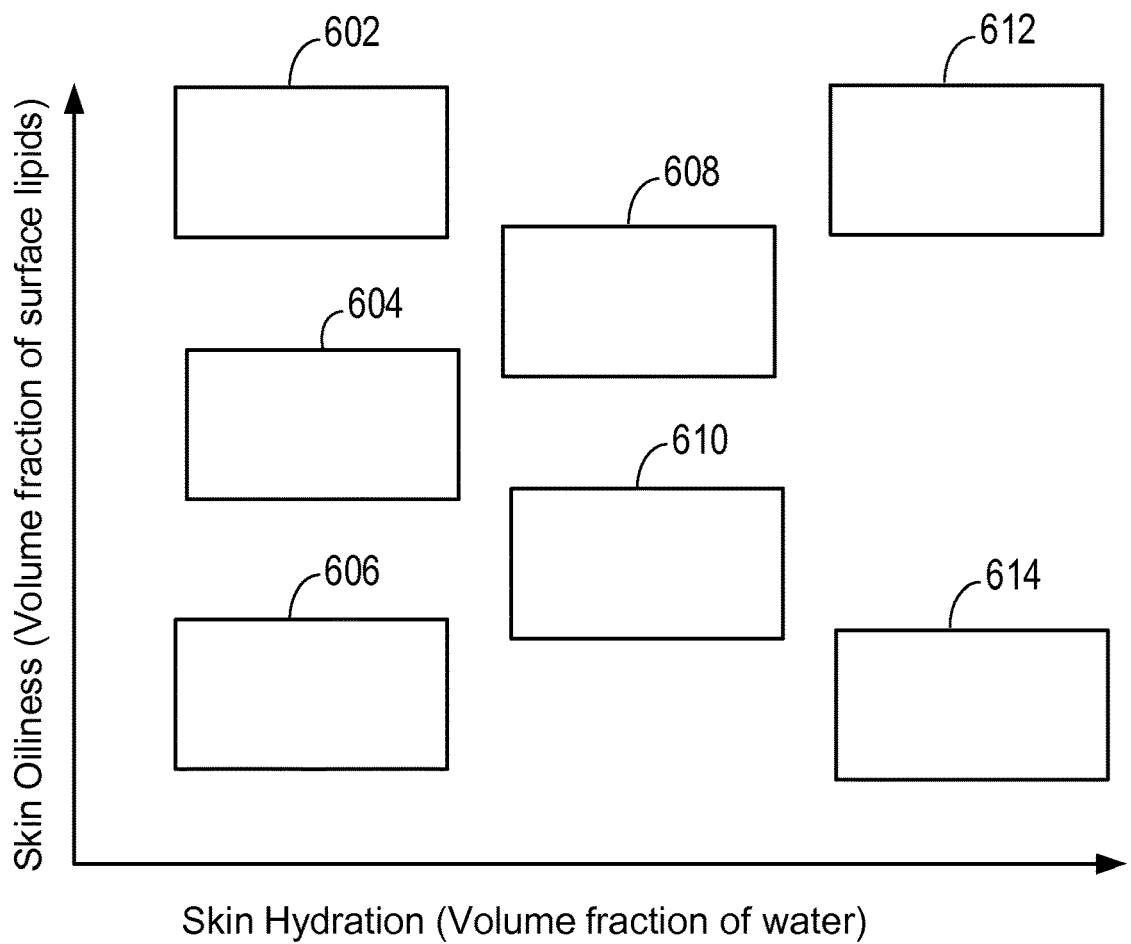
FIG. 6 illustrates relative lipid and water levels for various different skin conditions according to an embodiment.

Turning to FIG. 6, different combinations of water and lipid levels may further be associated with different skin conditions (e.g. dermatological conditions) according to some embodiments. Skin conditions such as atopic dermatitis show a drop in skin hydration level reflecting a drop of water holding capacity of the skin, increased transepidermal water loss (TEWL) and defects in barrier function. The same symptoms are seen in individuals suffering from psoriasis 606, eczema 614 and ichthyosis vulgaris 604. Nevertheless, these mentioned disorders show peculiar skin conditions with respect to the balance between hydration and oiliness. Eczema 614 leads to minor water loss (few percent) combined with noticeable lipid drop (~25%), whereas psoriasis 606 shows a dramatic decrease in hydration (~70%) and lipid (~40-70%) levels. Ichthyosis vulgaris 604 shows a decrease of hydration level (~63%) while the level of superficial skin lipids does not vary significantly (~±15%). Skin health is associated with the stability of the functioning of the skin barrier, which depends on the continuity of the skin's superficial lipids structure. Other skin conditions indicated in FIG. 6 include Seborrhea 602, acne vulgaris 612, contact dermatitis 608 and a drug eruption (e.g. allergy) 610.

Lipid phase behavior in the stratum corneum is considered to be crucial for the skin barrier function because skin superficial lipids have been found to serve as a water modulator in the stratum corneum. Thus, by determining the water and/or lipid level of skin in this way, it is possible for the system 100 to determine the condition of the skin and this can be used as an indicator of overall skin health. In some embodiments, the determined skin condition may be rendered (or provided, output or displayed) on a user interface.

In some embodiments, further to determining a skin condition based on the water or lipid level, the system 100 may be further configured to determine a recommendation for a skin treatment based on the determined skin condition. For example, if the system 100 determines that the water and/or lipid level is consistent with a skin condition (e.g. eczema), then the system 100 may recommend (or suggest) a topical cream, ointment or other treatment to improve the skin condition. In some embodiments, the determined recommendation may be rendered (or provided, output or displayed) on a user interface.

In some embodiments, the system 100 may be connected to a memory (e.g. a data storage device a database or server). For example, the connection may be a wired or wireless connection. In some of these embodiments, after having determined a skin condition and/or determined a recommendation for a skin treatment, the system 100 may be configured to send such determinations to the memory. In some embodiments, the system 100 may be configured to determine the lipid and/or water level of the skin at periodic intervals. In some of these embodiments, the system 100 may be configured to store the results at the memory. In this way, the system 100 may track a skin condition and/or determine improvement or change over time. The system 100 described herein can therefore quantitatively measure skin condition before and after treatment according to some embodiments, by taking into account the variation in skin hydration and lipid levels at different locations and also under different climatic variations.

The system 100 can provide a non-contact, portable, low cost and fast solution that has the capability to measure both lipid level and water level of skin. Thus, the system 100 has a dual modality. Furthermore, the storage of measured data can enable monitoring and control of a skin condition over time.

Figure 7:
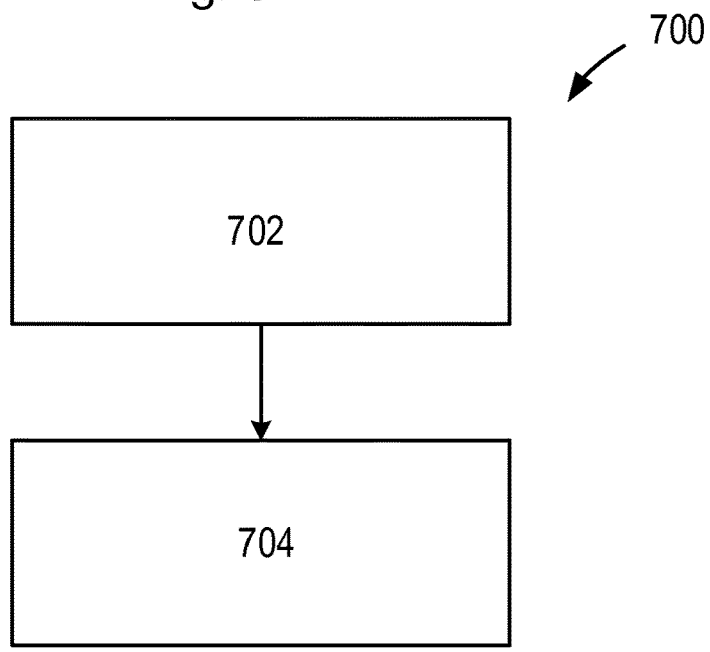
FIG. 7 is a flowchart of an example of a method of operating a system to determine a water or lipid level of skin according to an embodiment.

Turning now to FIG. 7, there is also provided a method 700 of operating a system 100 to determine a water or lipid level of skin. The system 100 is as described earlier. In particular, the system 100 comprises at least two electrodes 108 suitable for contacting skin and a signal generator 106 configured to generate an electrical signal across the at least two electrodes 108 at a frequency. At block 702, the method 700 comprises measuring a conductivity between the at least two electrodes 108. At block 704, the method 700 comprises determining a water or lipid level of skin based on the measured conductivity and the frequency of the electrical signal. Such steps were described as being performed by the system 100 and the details above will be understood to apply equally to method at blocks 702 and 704 of FIG. 7.

There is further provided a computer program product comprising a non-transitory computer readable medium, the computer readable medium having computer readable code embodied therein, the computer readable code being configured such that, on execution by a suitable computer or processor, the computer or processor is caused to perform any of the methods described herein.

It will thus be appreciated that the embodiments described herein also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions).

Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for determining a water and a lipid level of skin, the system comprising:
    at least two electrodes suitable for contacting skin; and
    a signal generator configured to generate an electrical signal at a frequency across the at least two electrodes,
    a conductivity measurement system for measuring the conductivity between the at least two electrodes, and
    a processor for processing an output of the conductivity measurement system,
    wherein the signal generator is configured to generate an electrical signal at a first frequency in a first frequency range and the system is configured to determine a water level of skin based on the measured conductivity when the frequency of the signal is the first frequency, wherein the first frequency range is a frequency range from 10 kHz to 100 kHz or a frequency range from 0.8

MHz to 5 MHz, wherein the first frequency range further comprises frequencies in which the contrast between the conductivities of (i) lipids and (ii) wet or dry skin is lower so that the skin conductivity is less sensitive to the lipid level; and wherein the signal generator is configured to generate an electrical signal at a second frequency in a second frequency range and the system is configured to determine a lipid level of skin based on the measured conductivity when the frequency of the signal is the second frequency, wherein the second frequency range is a frequency range from 10 Hz to 500 Hz or a frequency range from 10 MHz to 100 MHz, wherein the second frequency range further comprises frequencies in which the contrast between the conductivities of (i) lipids and (ii) wet or dry skin is higher so that the skin conductivity is more sensitive to the lipid level; and wherein the system is configured to:

measure a plurality of conductivities at a plurality of frequencies that comprise the first and second frequencies between the at least two electrodes, the conductivities measured at the first frequency being sensitive to and depending more on the water level than on the lipid level, and the conductivities measured at the second frequency being sensitive to and depending more on the lipid level than on the water level;

compare a measured conductivity of the plurality of measured conductivities to one or more predefined profiles describing the manner in which skin conductivity varies with frequency; and determine the water and the lipid level of skin based on the comparison of the measured conductivity and the frequency of the electrical signal to a corresponding profile of the one or more predefined profiles.

2. The system as claimed in claim 1, wherein the first frequency is 50 kHz or 1 MHz.

3. The system as claimed in claim 1, wherein the second frequency is 50 Hz or 50 MHz.

4. The system as claimed in claim 1, wherein the system is configured to determine the water and the lipid level of skin by determining an average water and an average lipid level of skin from the plurality of conductivity measurements.

5. The system as claimed in claim 1, wherein the system is further configured to: determine a skin condition based on the determined water or lipid level.

6. The system as claimed in claim 5, wherein the system is further configured to: determine a recommendation for a skin treatment based on the determined skin condition.

7. A method of operating a system to determine a water or lipid level of skin, the system comprising at least two electrodes suitable for contacting skin, a signal generator configured to generate an electrical signal across the at least two electrodes at a frequency, a conductivity measurement system for measuring a conductivity of skin between the at least two electrodes, and a processor for processing an output of the conductivity measurement system, the method comprising:

generating an electrical signal at a first frequency in a first frequency range, wherein the first frequency range is a frequency range from 10 kHz to 100 kHz or a frequency range from 0.8 MHz to 5 MHz, wherein the first frequency range comprises frequencies in which the contrast between the conductivities of lipids and wet or dry skin is lower so that the skin conductivity is less sensitive to the lipid level;

measuring a plurality of conductivities at a plurality of frequencies that comprise the first frequency between the at least two electrodes, the plurality of measured conductivities being sensitive to and depending more on the water level than on the lipid level;

generating an electrical signal at a second frequency in a second frequency range, wherein the second frequency range is a frequency range from 10 Hz to 500 Hz or a frequency range from 10 MHz to 100 MHz, wherein the second frequency range comprises frequencies in which the contrast between the conductivities of lipids and wet or dry skin is higher so that the skin conductivity is more sensitive to the lipid level; and measuring the plurality of conductivities at the plurality of frequencies that comprise the second frequency between the at least two electrodes, the plurality of measured conductivities being sensitive to and depending more on the lipid level than on the water level;

comparing a measured conductivity of the plurality of measured conductivities to one or more predefined profiles describing the manner in which skin conductivity varies with frequency; and determining the water and the lipid level of skin based on the comparison of the measured conductivity and the frequency of the electrical signal to a corresponding profile of the one or more predefined profiles.

8. A computer program product comprising a non-transitory computer readable medium, the computer readable medium having computer readable code embodied therein, the computer readable code being configured such that, on execution by a suitable computer or processor, the computer or processor is caused to perform the method as claimed in claim 7.

* * * * *